US008845553B2

(12) United States Patent
Brown

(10) Patent No.: US 8,845,553 B2
(45) Date of Patent: *Sep. 30, 2014

(54) TWISTED RIBBON WIRE GUIDEWIRE COIL

(71) Applicant: Abbott Cardiovascular Systems Inc., Santa Clara, CA (US)

(72) Inventor: Daniel G. Brown, Temecula, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/952,852

(22) Filed: Jul. 29, 2013

(65) Prior Publication Data
US 2013/0310708 A1 Nov. 21, 2013

Related U.S. Application Data

(62) Division of application No. 12/861,772, filed on Aug. 23, 2010, now Pat. No. 8,500,657.

(51) Int. Cl.
*A61B 5/00* (2006.01)
*A61M 25/00* (2006.01)
*A61M 25/09* (2006.01)

(52) U.S. Cl.
CPC ...... *A61M 25/09* (2013.01); *A61M 2025/09083* (2013.01); *A61M 2025/09191* (2013.01); *A61M 2025/09108* (2013.01)
USPC ...................................... 600/585

(58) Field of Classification Search
USPC ........................................ 600/585
See application file for complete search history.

(56) References Cited

U.S. PATENT DOCUMENTS

| 4,538,622 | A | 9/1985 | Samson et al. |
| 4,748,986 | A | 6/1988 | Morrison et al. |
| 4,932,419 | A | 6/1990 | de Toledo |
| 5,135,503 | A | 8/1992 | Abrams |
| 5,299,580 | A | 4/1994 | Atkinson et al. |
| 5,313,967 | A | 5/1994 | Lieber et al. |
| 5,341,818 | A | 8/1994 | Abrams et al. |
| 5,639,277 | A | 6/1997 | Mariant et al. |
| 6,139,511 | A | 10/2000 | Huter et al. |
| 6,451,026 | B1 | 9/2002 | Biagtan et al. |
| 6,482,166 | B1 | 11/2002 | Fariabi |
| 6,638,267 | B1 | 10/2003 | Esselstein et al. |
| 6,666,829 | B2 | 12/2003 | Cornish et al. |
| 6,818,076 | B1 | 11/2004 | Farzin-Nia |
| 6,881,194 | B2 | 4/2005 | Miyata et al. |
| 7,168,117 | B2 | 1/2007 | Gladney et al. |
| 7,201,344 | B2 | 4/2007 | Higeta |
| 8,500,657 | B2 * | 8/2013 | Brown .......................... 600/585 |

OTHER PUBLICATIONS

Glossary of Spring Terminology at http://www.patrickmfg.com/glossary2.htm, dated Jun. 28, 2010.

* cited by examiner

*Primary Examiner* — Brian Szmal
(74) *Attorney, Agent, or Firm* — Fulwider Patton LLP

(57) ABSTRACT

A medical guidewire having distal tip coil that includes a twisted ribbon wire construction. The distal tip coil is mounted to the distal end of the distal core section of the guidewire. The coil is made from a flat ribbon wire with a polygonal, preferably rectangular, cross-section that is twisted along the length of the wire. The twisted, flat ribbon wire creates a tip coil that has a roughened, undulating surface at the outer circumference that, whether coated or bare, is perceptible to the physician or cardiologist when pushing or torquing the guidewire in an interventional procedure.

1 Claim, 5 Drawing Sheets

TWISTED RIBBON WIRE GUIDEWIRE COIL

This application is a division of co-pending U.S. Ser. No. 12/861,772 filed Aug. 23, 2010, the entire contents of which are hereby incorporated by reference.

BACKGROUND

This invention relates to the field of medical guidewires for advancing intraluminal devices such as stent delivery catheters, balloon dilatation catheters, atherectomy catheters and the like within body lumens.

The most common method for insertion of percutaneous catheters is the Seldinger technique. In this procedure, a local anesthesia is delivered and a skin puncture is made proximal to the femoral or brachial artery with an obturator positioned within a cannula (sheath). Once inside the artery, the obturator is removed and a guide catheter placed into the desired position in the anatomy through the cannula. Then a guidewire is inserted through the cannula into the artery. The guidewire is then advanced into the vasculature guided by fluoroscopic imaging to the desired site. Generally, the distal tip of the guidewire is pre-shaped by manufacture or has the ability to be shaped by the physician in order to steer the guidewire to the desired location by rotating and advancing in combination. Once the guidewire is at the desired treatment site, a diagnostic or therapeutic catheter is advanced over the guidewire, and the desired procedure is performed.

Further details of guidewires and devices associated therewith for various interventional procedures can be found in, for example, U.S. Pat. No. 4,748,986 (Morrison et al.); U.S. Pat. No. 4,538,622 (Samson et al.): U.S. Pat. No. 5,135,503 (Abrams); and U.S. Pat. No. 5,341,818 (Abrams et al.); which are hereby incorporated by reference in their entirety.

Because of the environment that guidewires are used in, and the purpose they serve, it is desirable to have several basic features for most, if not all, guidewires. The guidewire must navigate and advance within the lumens of a patient, coming into contact with delicate tissue. For this reason, the guidewire requires a soft, flexible distal tip which can be manipulated without causing injury to the vessel walls. Also, it must be sufficiently maneuverable to reach the required destination, which requires stable torsional characteristics, and a rigid proximal shaft that can be pushed to advance the guidewire. These characteristics are difficult to achieve, as one tends to negate the other. It is also desirable for the outer diameter of the guidewire to fit properly within the inside diameter of the lumen within which it is disposed. This can be problematic for guidewires designed for the peripheral arteries, such as those found within the legs and arms, because the size of the diagnostic and therapeutic devices used in these arteries are typically large, requiring a larger outer diameter guidewire, which can be stiffer and less flexible than coronary wires due to its size. In addition, because the guidewire is steered to the desired location within the vasculature under fluoroscopy, a radiopaque marker of some type is required, which is typically made from a precious metal coil, band or solder.

Conventional guidewires for angioplasty, stent delivery, atherectomy and other vascular procedures usually have an elongate core with one or more tapered sections near the distal end thereof and a flexible body such as a helical coil or a tubular body of polymeric material disposed about the distal portion of the core. A shapeable member, which may be the distal end of the core or a separate shapeable ribbon, is secured to the distal end of the core and extends through the flexible body, and is connected to the distal end of the flexible body by soldering, brazing, or welding, which forms a rounded distal tip. Torquing means are provided on the proximal end of the core to rotate, and thereby steer, the guidewire while it is being advanced through a patient's vascular system. The leading distal tip is highly flexible and atraumatic so it does not damage or perforate the vessel, and the portion behind the distal tip is increasingly stiff which better supports a balloon catheter or similar device.

SUMMARY OF THE INVENTION

The present invention is directed to an intraluminal medical guidewire, comprising a solid, cylindrical core having at least a partially tapered distal core section and a proximal core section; a first coil having a constant outside diameter mounted to the tapered distal core section, wherein the first coil is a single strand of a generally flat ribbon wire having a longitudinal axis that is twisted about the longitudinal axis over a length of the flat ribbon wire, and wherein the single strand further includes a plurality of turns to form a helix; a second coil having a constant outside diameter with a coil wire having a cylindrical wire shape mounted to the distal core section proximal of the first coil; and a polymer coating at least partially covering the first coil and the coated first coil has in at least one turn an undulating circumferential profile.

In another alternative embodiment, the intraluminal medical guidewire includes a twist in both the first and second coils, which are comprised of a single strand of a generally flat ribbon wire having a longitudinal axis that is twisted about the longitudinal axis over a length of the flat ribbon wire, and wherein the single strand further includes a plurality of turns to form a helix.

In another alternative embodiment, the intraluminal medical guidewire includes a first coil having a constant outside diameter with a coil wire having a cylindrical wire shape mounted to the distal core section; and a second coil comprised of a single strand of a generally flat ribbon wire having a longitudinal axis that is twisted about the longitudinal axis over a length of the flat ribbon wire, and wherein the single strand further includes a plurality of turns to form a helix; and a polymer coating at least partially covering the first coil;

In various alternative embodiments, the intraluminal medical guidewire includes a twist in the coil wire that is uniform from one end of the first distal coil to an opposite end of the first distal coil. The distal core section may include one or more tapers. The intraluminal medical guidewire may have the twisted first distal coil positioned at a distal-most location of the distal core section.

Further, the intraluminal medical guidewire in various alternative embodiments may include a width of the coil wire that is about 0.00075 in.-0.0030 in.; a twisted first distal coil with an outside diameter of about 0.035 in.-0.010 in.; a rectangular cross-section of the twisted first distal coil that undergoes about 2-8 rotations of 360° over a length of circumference of the first distal coil as measured by ¼ ($\pi$)(D) where D is the diameter of the helix; and the turns of the twisted first distal coil that undergo 1-10 turns of 360°/mm length of the coil wire. Also, the rectangular cross-sectional shape of the twisted coil may include a height-to-width aspect ratio of about 1:2, 1:3, or 2:3. These specific dimensions, values, and features are the result of accumulated empirical analyses and observations applied to address the engineering requirements in medical guidewires and are well beyond routine experimentation.

In still further alternative embodiments, the twisted distal coil of the guidewire may have turns that are overlapping, tightly packed without space therebetween, or spaced apart, or a combination thereof. And in another embodiment, the rectangular cross-sectional shape rotates in the same direction from one end of the coil to the other.

The twisted, flat ribbon coil even when covered with one or multiple polymeric coating layers still retains its undulating circumferential profile. When the physician or cardiologist advances and torques the guidewire at the proximal end, the undulating surface profile at the distal end of the guidewire as it moves along the interior of the vessel provides precise, tactile feedback to its user. This enables the physician or cardiologist to more precisely maneuver and deftly negotiate a patient's tortuous vasculature to ultimately locate the guidewire accurately and more easily at the treatment site. This improved feel is highly valued and useful to cardiologists and physicians who use such guidewires in the field.

Typically, the tip coil only serves to add a uniform profile and form an atraumatic surface to the otherwise rigid and irregularly shaped, floppy distal end of the guidewire core. On the other hand, the present invention twisted, flat ribbon wire coil adds mass to the coil leading to a stronger coil. A stronger coil enables designers and engineers to remove mass and reduce the size of the guidewire core. A lower mass or a slimmer guidewire core at its distal end, even though still pushable as before, now has a distal core section that is even more gentle and atraumatic to minimize possible injury to the vessel intima. Furthermore, when the mass of the guidewire is shifted to the coil, the distal core section can incorporate engineering improvements such as a parabolic grind to impart a linear change in stiffness. The linear change in stiffness at the distal end of the guidewire then enhances the ability of the cardiologist to precisely control and manipulate the distal end.

The present invention twisted, flat ribbon wire coil in adding mass to the coil allows for greater variation in the range of tip stiffnesses beyond what would be normally achievable using the conventional methods of changing the core grind or materials.

DETAILED DESCRIPTION OF THE PREFERRED EMBODIMENTS

Figure 1:
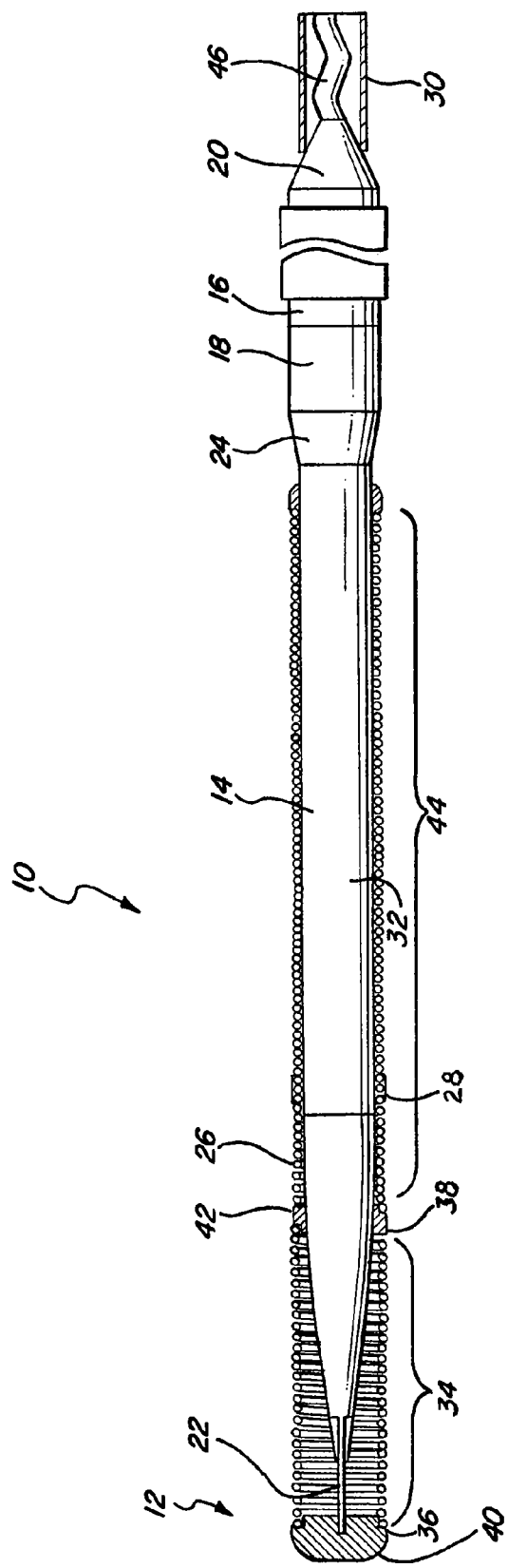
FIG. 1 is a side elevational view of the present invention twisted ribbon coil as mounted to a guidewire.

In FIG. 1, a guidewire 10 with a distal tip 12 is shown which has features of a preferred embodiment of the present invention. The guidewire 10 has an elongate core 14 with a proximal core section 16 and a distal core section 18. The proximal core section 16 terminates proximally in a proximal end 20, and the distal end terminates in a distal end 22. The distal end 22 preferably has a substantially round cross-section, but in the embodiment shown, is flattened and is malleable in order to facilitate shaping of the distal tip of the guidewire 10 by the user. The proximal core section 16 of the elongate core member 14 can have an outer diameter of about 0.017 inch (0.4 mm) to about 0.030 inch (0.8 mm), but preferably has an outer diameter of about 0.020 inch (0.5 mm) to about 0.027 inch (0.7 mm).

The elongate core 14 may be formed of stainless steel, specifically 304V stainless steel, pseudoelastic or superelastic nickel-titanium (NiTi) alloys, or combinations thereof such as described in U.S. Pat. No. 5,341,818 (Abrams et al.) which has been incorporated by reference. Other materials may also be used such as high strength alloys described in U.S. Pat. No. 6,482,166 (Fariabi), titled HIGH STRENGTH MEMBER FOR INTRACORPOREAL USE which is incorporated herein by reference in its entirety. In the preferred embodiment, the distal core section 18 is made from a pseudoelastic/superelastic NiTi alloy, while the proximal core section 16 is made from stainless steel as described above. The two sections 16, 18 are joined together by welding, soldering, adhesive bond, a linking hypotube, and/or a mechanical joint or fastener.

The elongate core 14 may be coated, at least in part, with a lubricious coating such as a fluoropolymer, e.g., TEFLON® available from DuPont. Another coating that may be used is a MICROGLIDE® coating. Hydrophilic coatings may also be used to cover all or portions of the elongate core 14.

The distal core section 18 has a first tapered segment 24 and a second tapered segment 26, wherein the elongate core 14 tapers along its length distally to a reduced diameter, thereby increasing the flexibility of the core in a distal direction. The second tapered segment 26 may have a straight taper as seen with the first tapered segment 24, or may have a parabolic grind that produces a linear change in stiffness of the core. This technology is disclosed in, for example, U.S. Pat. No. 6,666,829 (Cornish et al.), the entire contents of which are incorporated by reference. As seen in FIG. 1, the second tapered segment 26 has a curvilinear profile versus the straight tapered profile of the first tapered segment 24.

To be more visible under fluoroscopy, the second tapered segment 26 of the distal core section 18 of the elongate core 14 is marked with a radiopaque marker 28; sometimes the first tip coil can also be made with a radiopaque material. The marker 28 can be a band made of radiopaque material or in this case, gold solder is used. A removable radiopaque marker 30 is located at the proximal end 20. Other markers at various locations may be used in alternative embodiments. The markers 28, 30 are preferably made of a radiopaque metal such as gold or tantalum, but may be made of any suitable radiopaque material, such as bismuth or barium. The markers 28, 30 are preferably attached to the elongate core 14 by soldering, brazing, bonding with an adhesive such as epoxy or cyanoacrylate, or by mechanically crimping in place.

Generally, the markers have a cross-sectional thickness of about 0.0005 inch (0.013 mm) to about 0.004 inch (0.1 mm), preferably about 0.001 inch (0.025 mm) to about 0.002 inch (0.05 mm); a width of about 0.010 inch (0.25 mm) to about 0.10 inch (2.5 mm), preferably about 0.030 inch (0.76 mm) to about 0.070 inch (1.8 mm), and more preferably about 0.050 inch (1.3 mm).

The first tapered segment 24 and second tapered segment 26 can be adjacent, but preferably are separated by a constant diameter segment 32 that is disposed between the first tapered segment and the second tapered segment. The outer diameter of the constant diameter segment 32 can be about 0.008 inch (0.2 mm) to about 0.014 inch (0.36 mm), but is preferably about 0.009 inch (0.23 mm) to about 0.013 inch (0.33 mm), and more preferably about 0.010 inch (0.25 mm) to about 0.012 inch (0.3 mm).

At the proximal end 20 of the elongate core 14 is an optional dock exchange system 46 to allow attachment and detachment of an extension guidewire or other suitable medical device (not shown). Such a dock exchange system 46 is disclosed in, for example, U.S. Pat. No. 6,451,026 (Biagtan et al.), and U.S. Pat. No. 6,638,267 (Esselstein et al.), the entire contents of which are incorporated by reference herein. The dock exchange system 46 features an insert that frictionally fits or mechanically interlocks with a receiving socket or hypotube in the extension guidewire.

Still in FIG. 1, a distal tip coil 34, which has a proximal end 38 and a distal end 36, is disposed around at least a portion of the distal core section 18 of the elongate core 14. The distal tip coil 34 is preferably made from a single strand of flat ribbon wire that is twisted along its length and then wound around a mandrel into a helix. The flat ribbon wire preferably has a substantially rectangular cross-section that rotates 360° about the coil wire axis to create the twist. The substantially rectangular cross-section of the ribbon wire can have a thickness of about 0.002 inch (0.05 mm) to about 0.006 inch (0.15 mm), preferably about 0.003 inch (0.08 mm) to about 0.005 inch (0.13 mm). The width of the rectangular cross-section of the wire can be about 0.006 inch (0.15 mm) to about 0.018 inch (0.46 mm), preferably about 0.010 inch (0.25 mm) to about 0.014 inch (0.36 mm), and more preferably about 0.011 inch (0.28 mm) to about 0.013 inch (0.33 mm).

The outer diameter of the distal tip coil 34 can be about 0.018 inch (0.76 mm) to about 0.040 inch (1 mm), preferably about 0.03 inch (0.76 mm) to about 0.037 inch (0.94 mm). The length of the distal tip coil 34 can be from about 20 inches (50 cm) to about 55 inches (140 cm), preferably about 31.5 inches (80 cm) to about 45 inches (115 cm), and more preferably about 35 inches (90 cm) to about 39 inches (100 cm).

The distal end 36 of the distal tip coil 34 is preferably attached to the distal end 22 of the elongate core 14 by a solder ball, nose cone, or the like. The proximal end 38 of the distal tip coil 34 is preferably joined to the core with solder, braze, adhesive, and/or a mechanical joint 42.

Proximal of the distal tip coil 34 is an optional proximal coil 44. The distal tip coil 34 and/or the proximal coil 44 can be one continuous, integral coil, or two or more abutting coils. The distal and proximal ends of the proximal coil 44 can be joined to the elongate core 14 by solder, braze, adhesive, and/or mechanical joint. Further, the proximal coil 44 as shown in FIG. 1 is made from a wire with a circular cross-sectional shape. The twisted ribbon wire from the distal tip coil 34 may be used in a portion or all of the proximal coil 44 as well. In an alternative embodiment, the distal tip coil 34 may be made from a first and second distal tip coils of twisted wire ribbon, as generally represented by FIG. 1. Or the distal tip coil may be made from a first distal tip coil made from twisted wire ribbon, then a second distal tip coil made from standard round wire.

In an alternative embodiment, one or more intermediate distal coils may be located between the distal and proximal coils 34, 44. In such an embodiment, the guidewire includes one or more intermediate distal coil mounted to the distal core section in between the first coil and the second coil, and the intermediate distal coil includes a single strand of a coil wire with a rectangular cross-sectional shape with a height and a width, wherein the rectangular cross-sectional shape rotates 360° about a longitudinal axis of the coil wire and along a length of the coil wire to create a continuous twist, wherein the coil wire includes a plurality of spaced apart turns forming a helix. The intermediate distal coil may have a constant outside diameter.

Figure 2:
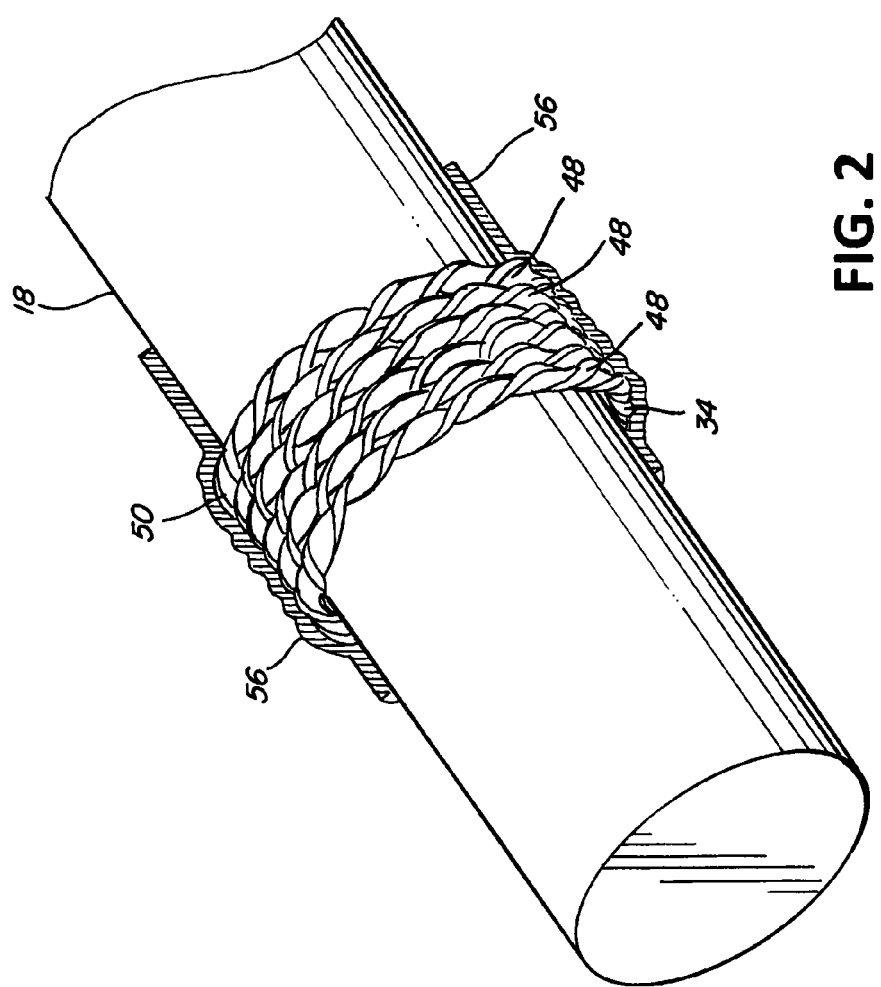
FIG. 2 is an enlarged isometric view of a preferred embodiment twisted ribbon coil.
Figure 3:
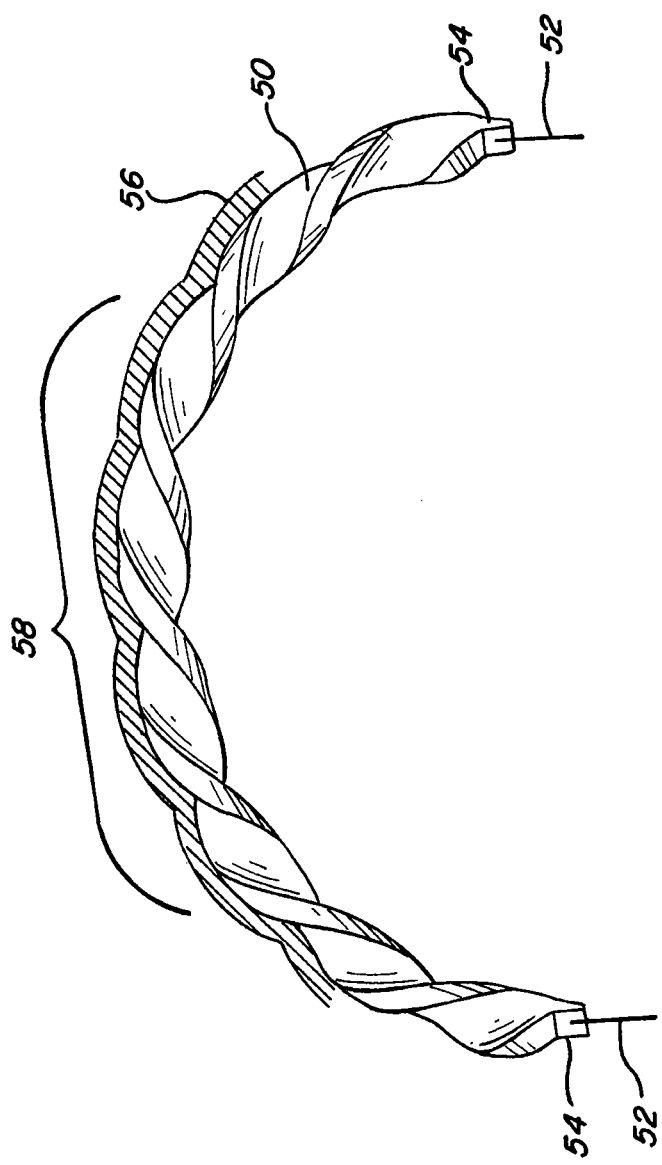
FIG. 3 is an enlarged detail view of one-half of a single turn of a twisted ribbon coil.
Figure 7:
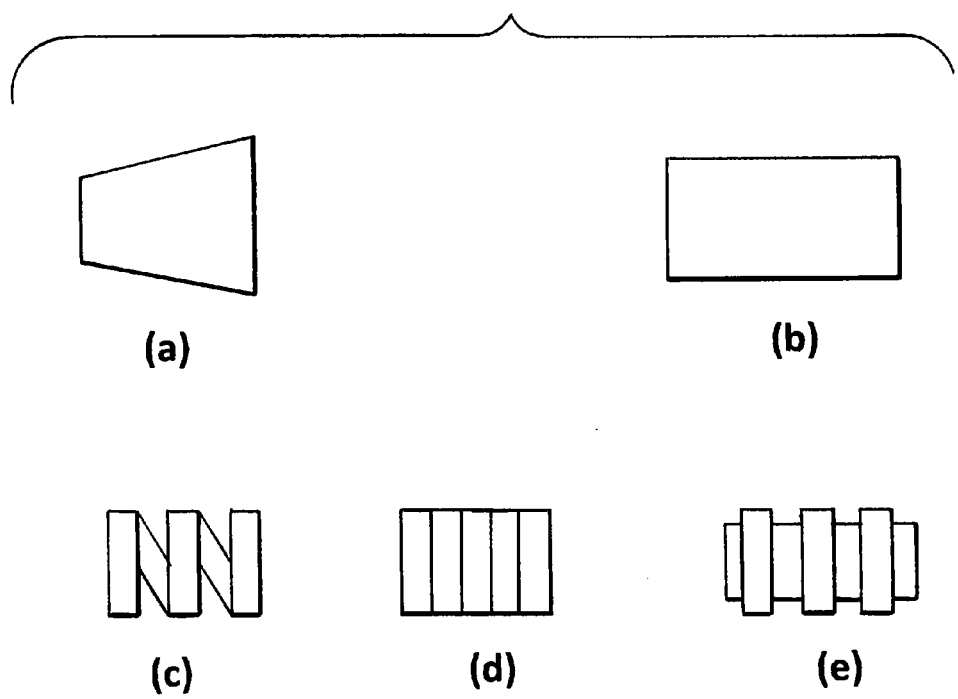
FIG. 7 are simplified schematic side elevational views of a flat ribbon coil that: (a) is tapered, (b) has a constant OD, (c) has spaced apart turns, (d) has tightly packed turns, and (e) has overlapping turns.

FIG. 2 is an magnified detail view or a portion of the distal tip coil 34 as it is mounted to the distal core section 18. Certain features are omitted or incomplete, and are not shown to scale in the drawing for the sake of clarity. As seen in FIGS. 2 and 7, the distal tip coil 34 is a wire wound into a coiled helix with a number of turns 48 with each turn abutting each other as shown, or they may be spaced apart, overlapping, or a combination thereof. FIG. 3 is a magnified detail view of 180° of a single turn 48 of the coil 34. As seen here, the wire 50 is preferably a twisted ribbon having a rectangular cross-section 54 that rotates 360° about a central axis 52 of the wire and along the length of the wire 50. In the preferred embodiment, the rectangular cross-section 54 of the distal tip coil 34 undergoes about 2-8 rotations of 360° over a length of circumference of the distal tip coil 34 as measured by ¼ (π)(D) where D is the diameter of the coil 34. This parameter defines sufficient twist in the wire 50 for irregularities at the coil circumference, yet the twists are not too densely packed so that one or more polymer coatings 56 thereon settle into the grooves of the twist to maintain a undulating circumferential profile 58, as best seen in the axial end view of the tip coil 34 of FIG. 3. In an alternative embodiment, the turns of the twisted distal tip coil 34 undergo 1-10 turns of 360°/mm length of the coil wire.

In a single wire turn, this undulating circumferential profile 58 in the polymer coating 56, or without any polymer coating with a bare surface of the wire, does not exist in a conventional guidewire coil having a circular cross-section wire, which is completely smooth. The undulating circumferential profile 58, seen in coil end view of FIG. 3, within each turn 48 of the twisted ribbon wire gives the cardiologist or physician improved feel for controlling and maneuvering the distal end of the guidewire 10 during intravascular procedures. Because the undulating circumferential profile 58 is along the circumference of the coil 34, any torquing of the guidewire by the cardiologist causes the undulating circumferential profile 58 to rotate and slide against the intima of a patient's vessel, which gives the cardiologist valuable tactile feedback. In contrast, the smooth outer circumference of a common, round-wire coil cannot provide such level of tactile feedback.

The twisted distal tip coil 34 also provides improved tactile feedback to the physician when pushing or advancing the guidewire 10, again due to the circumferential undulating profile 58, and the effect of the uneven, roughened, undulating surface in a direction along the central axis of the guidewire 10 and coil 34. Finally, as seen in FIG. 2, looking at the tip coil 34 in a side profile reveals uneven, undulations from the turns and twists which provide a roughened surface texture to the outer circumference of the coil 34 regardless of whether it is coated or not coated. Thus, tactile feedback to the physician is enhanced while the guidewire 10 is steered and pushed along the patient's vasculature.

The twisted ribbon coil 34 creates a highly roughened, undulating surface that is on a scale that is much more physically perceptible to the cardiologist or physician as compared to, for example, a textured surface finish on a coating covering the guidewire core. Yet the roughened, undulating surface of the twisted ribbon coil 34 is still minute and subtle so not to traumatize tissue in the vessel. Also, the location of the roughened outer circumferential surface is at the very distal-most tip coil 34, versus a roughened coating covering the guidewire core that is proximal of the tip coil 34. As a result, being located at the very leading distal end of the guidewire 10 ensures that the physician can feel and control the very distal tip 12 of the guidewire 10, which is especially useful in crossing difficult lesions.

Figure 6:
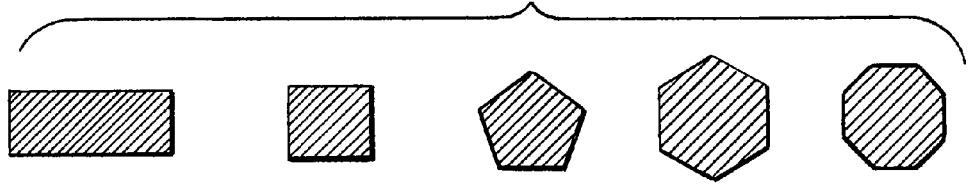
FIG. 6 are cross-sectional views of coil ribbon wires having different shapes.

Accordingly, the rectangular cross-section has a height dimension and a width dimension, wherein the width of the coil wire is preferably about 0.00075 in.-0.0030 in., and the rectangular cross-sectional shape includes a preferable height-to-width aspect ratio of about 1:2, 1:3, or 2:3. FIG. 6 shows in cross-section some of the preferred polygonal shapes for the coil wire. This includes a rectangle, a square, a pentagon, a hexagon, and a polygon with many flat outer surfaces. The number of flat outer surfaces and their dimensions affect the roughness or degree of irregularity in the outer circumference of the tip coil, and hence the feel perceived by the cardiologist or physician.

It is preferable that the rate of twist in the coil wire 50 is uniform from one end of the distal tip coil 34 to an opposite end of the coil. As seen in FIG. 1, the twisted distal tip coil 34 is preferably positioned at a distal-most location of the distal core section 18. The twisted ribbon wire portion of a coil may be joined to a round/cylindrical wire coil; they may be separate coils as generally represented in FIG. 1; or they may have alternate turns or coils of ribbon-round-ribbon-round, etc. The outside diameter of the distal tip coil is preferable constant, or it may be tapered as seen in the side elevational views of FIGS. 7(*a*), 7(*b*).

The inside diameter of the distal tip coil 34 is preferably spaced from the outside diameter of the elongate core 14. The distal tip coil 34 is preferably made of a biocompatible material such as stainless steel, specifically, 304V stainless steel, but may be made from any suitable material having appropriate mechanical properties such as Co—Ni—Cr—Mo alloys (e.g., MP35N) or NiTi alloy, which can have pseudoelastic or shape memory characteristics, or both in combination. Furthermore, the distal tip coil 34 may be preferably made of a stainless steel, or a radiopaque metal such as platinum, nickel, iridium, palladium, rhenium, tantalum, gold, or alloys thereof. The distal tip coil 34 as mentioned above may be polymer coated 56, at least in part, with a lubricious coating such as a fluoropolymer, e.g., TEFLON® available from DuPont, or MICROGLIDE® coating. Hydrophilic coatings may also be used.

The proximal coil 44 is formed from a wire material that is preferably round in cross-section, and is preferably radiolucent. However, either or both of the coils 34, 44 may be radiopaque or radiolucent, or may be combined into a single helical coil of material with substantially rectangular and round cross-sections.

Figure 4:
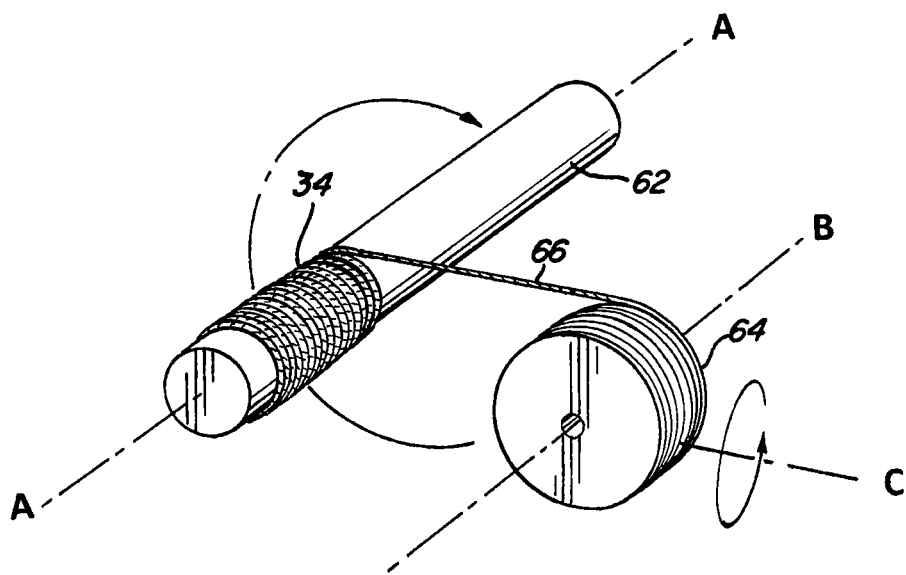
FIG. 4 is a schematic view of one method of adding a twisted ribbon coil to a guidewire core.
Figure 5:
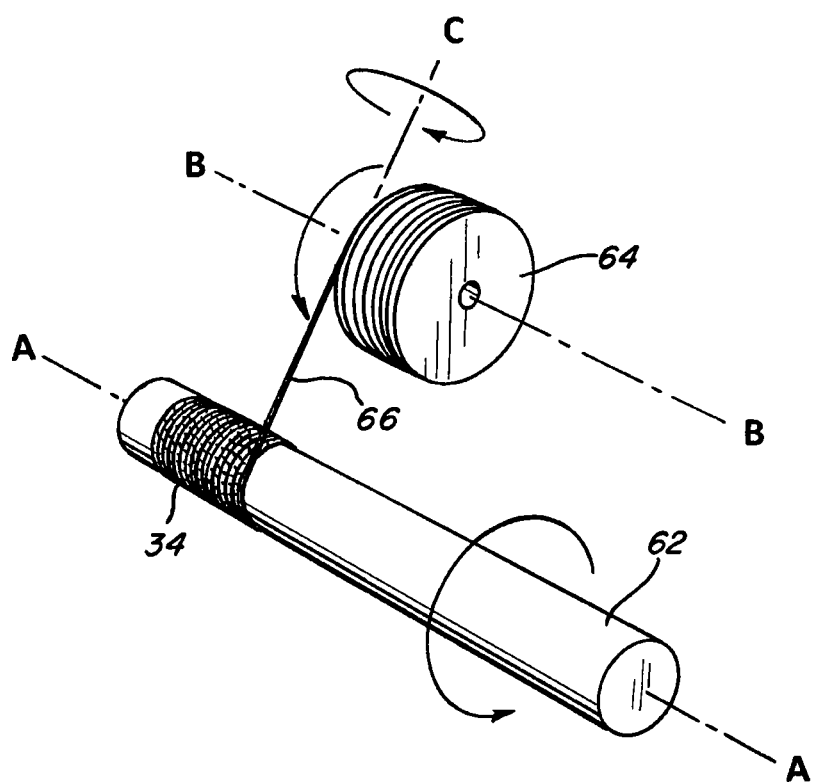
FIG. 5 is a schematic view of an alternative method of adding a twisted ribbon coil to a guidewire core.

FIGS. 4 and 5 are schematic depictions of two preferred methods for adding a twisted ribbon coil to a guidewire core. To ensure clarity of illustration, the motors, linkages, and production machinery are omitted from the schematic drawings of FIGS. 4 and 5.

FIG. 4 shows a section of a stationary guidewire core 62 having a longitudinal axis A, and a wire supply reel or spool 64 with its own axis B. The spool 64 has a single strand winding of wire 66 to be transferred to the guidewire core 62 to create the tip coil 34.

To do this, a free end of the single strand coil wire 66 is first anchored to the guidewire core 62. The spool 64 is then moved continuously about axis A of the guidewire core 62 (path indicated by curved arrow). Each 360° revolution of the spool 64 around axis A adds another turn to the tip coil 34. The process is akin to wrapping a first-aid bandage around an injured limb. As seen in FIGS. 7(*c*)-7(*e*), the turns may be overlapping, spaced apart, tightly packed together, or a combination thereof, depending on the rate of linear translation of the spool 64 along the shaft of the guidewire core 62.

The wire 66 is preferably a flat ribbon with a rectangular or polygonal shape cross-section. To impart the twist in the single strand, flat ribbon wire 66, during each revolution around axis A, the spool 64 simultaneously revolves about axis C, which axis C is parallel to or coincides with the axis of the wire 66. The faster the spool 64 revolves about wire axis C per unit rate of revolution of the spool 64 about core axis A, the tighter the twist; the slower the spool 64 revolves about axis C, the resulting twist will be looser and more spread out. Multiple strand wires are not used here, because the spool 64 rotating about wire axis 66 will entangle the wires. Also, multi-strand wires further needless complicate the creation of the twisted ribbon coil during manufacturing and increase cost.

As understood to those skilled in the art from FIG. 4, the greater the tension in wire 66, the more tightly wrapped the coil 34 will be on to the guidewire core 62, and vice versa. When the desired number of turns in the coil 34 is reached, the wire 66 is detached from the spool 64 and anchored to the guidewire core 62.

FIG. 5 is an alternative method for adding a tip coil 34 to a guidewire core 62. In this embodiment, the guidewire core rotates about its own longitudinal axis A (as indicated by the curved arrow). The free end of a single strand of the coil wire 66 is first anchored to the guidewire core 62. Next, as the core 62 spins about axis A, the strand of coil wire 66, as fed from the free-turning spool 64, begins to wrap itself around the core 62. The spool 64 simultaneously moves linearly along the shaft of the guidewire core 62 to create overlapping, tightly packed, spaced-apart turns in the coil 34, or a combination thereof.

As the foregoing process is taking place, the spool 64 rotates about axis C, which is parallel to or coincides with the axis of the wire 66. As with the FIG. 4 embodiment, because a flat ribbon wire is used, the rotation about the wire axis C imparts a twist to the wire 66.

The guidewire 10 may have an optional shaping ribbon similar to that described in U.S. Pat. No. 5,135,503 (Abrams), which is incorporated by reference herein. The shaping ribbon extends distally from the distal end of the distal core section 18. The shaping ribbon has a length of about 1 cm to about 7 cm, preferably about 3 cm to about 5 cm. It is preferably flat-ended, but may also have a round cross-section with an outer-diameter of about 0.002 inch to about 0.006 inch, preferably about 0.003 inch to about 0.005 inch, and more preferably about 0.004 inch. The shaping ribbon is preferably made of a biocompatible, malleable material that can be plastically deformed under finger pressure, such as stainless steel, specifically 304V stainless steel. It may also be made from any suitable material having the appropriate mechanical properties such as Co—Ni—Cr—Mo alloys (e.g., MP35N) or a NiTi alloy. Finally, the shaping ribbon may be a separate, discrete structure that is joined to the distal end of the distal core section 18, or it may be an integral extension 22 from the distal tip of the distal core section 18 as in FIG. 1.

In various preferred embodiments, the guidewire 10 can be from about 43 inches (110 cm) to about 140 inches (355 cm) in overall length, but is preferably about 55 inches (140 cm) to about 122 inches (310 cm) in length. In addition, the guidewire 10 has further preferred embodiments having overall lengths of about 57 inches (145 cm), about 75 inches (190 cm), and about 118 inch (300 cm).

Unless otherwise described herein, conventional materials and manufacturing methods may be used to make the present invention. Additionally, various modifications may be made to the present invention without departing from the scope thereof. Although individual features of embodiments of the invention may be shown in some of the drawings and not in others, those skilled in the art will recognize that individual features of one embodiment of the invention can be combined with any or all of the features of another embodiment.

I claim:

1. An intraluminal medical guidewire, comprising:
a solid, cylindrical core having a distal core section with a distal end and a proximal end, the proximal end transitioning to a proximal core section;
a first distal coil mounted to the distal core section, the first distal coil having:
a single strand of a coil wire with a rectangular cross-sectional shape with a height and a width, wherein the rectangular cross-sectional shape rotates 360° about a longitudinal axis of the coil wire and along a length of the coil wire to create a continuous twist,
wherein the coil wire includes a plurality of turns forming a helix having a constant outside diameter;
a second distal coil having a coil wire mounted to the distal core section proximal of the first distal coil; and
a polymer coating partially covering the first distal coil.

* * * * *